United States Patent [19]
Wolleb et al.

[11] Patent Number: 5,641,879
[45] Date of Patent: Jun. 24, 1997

[54] PHTHALOCYANINES SUBSTITUTED BY PHOSPHORUS-CONTAINING GROUPS

[75] Inventors: Heinz Wolleb, Marly; Hanspeter Preiswerk, Birsfelden; Beat Schmidhalter, Giffers; Heinz Spahni, Frenkendorf, all of Switzerland

[73] Assignee: Ciba-Geigy Corporation, Tarrytown, N.Y.

[21] Appl. No.: 530,971

[22] Filed: Sep. 20, 1995

[30] Foreign Application Priority Data

Sep. 23, 1994 [CH] Switzerland ............... 2907/94

[51] Int. Cl.$^6$ ................................................ C07D 487/22
[52] U.S. Cl. ................................... 540/128; 540/122
[58] Field of Search ....................................... 540/128

[56] References Cited

U.S. PATENT DOCUMENTS

| 5,064,951 | 11/1991 | Yamaeski ............... 540/128 |
| 5,149,847 | 9/1992 | Yamasaki ............... 540/128 |
| 5,283,094 | 2/1994 | Sasakawa et al. ....... 428/64 |

FOREIGN PATENT DOCUMENTS

| 0373643 | 6/1990 | European Pat. Off. . |
| 0391415 | 10/1990 | European Pat. Off. . |
| 0511598 | 11/1992 | European Pat. Off. . |
| 0513370 | 11/1992 | European Pat. Off. . |
| 0600427 | 6/1994 | European Pat. Off. . |

OTHER PUBLICATIONS

Y. Xu et al., Palladium-Catalysed Synthesis of Alkylarylphenyl-Phosphine Oxides, pp. 781–782, (1989 Nov.).
M. Emmelius et al., Angewandte Chemie, pp. 1475–1502, (1989 Nov.).

*Primary Examiner*—Mukund J. Shah
*Assistant Examiner*—Pavanaram K. Sripada
*Attorney, Agent, or Firm*—Michele A. Kovaleski; Luther A. R. Hall

[57] ABSTRACT

The invention relates to phthalocyanines and metal complexes thereof with divalent metals or divalent oxo metals, which contain at least one phosphorus-containing substituent bonded to the peripheral carbon skeleton via the phosphorus atom.

The compounds preferably conform to the general structural formula $(G)_k$-A-$(Q)_l$, in which A is a phthalocyanine or metal complex thereof with a divalent metal or a divalent oxo metal, G is a phosphorus-containing substituent, Q is a further substituent as defined below, the index k is a number from 1 to 16, and l, independently thereof, is 0 or a number from 1 to 15, with the proviso that the sum of k and l is a number less than or equal to 16.

The invention also relates to a material for the optical recording and storage of information, in which at least one storage layer (2) of a novel phthalocyanine compound or a metal complex thereof has been applied to a transparent, dielectric carrier material (1).

25 Claims, No Drawings

PHTHALOCYANINES SUBSTITUTED BY PHOSPHORUS-CONTAINING GROUPS

The invention relates to phthalocyanines substituted by phosphorus-containing groups, to their preparation, and to their use in storage layers of optical information carriers.

The use of dyes which absorb radiation in the near infra-red (NIR) region for recording information in WORM (write once read many) systems has been known for some time and is described, for example, by M. Emmelius in Angewandte Chemie, Issue 11, pages 1475–1502 (1989). The change in absorption which is necessary for recording information in the form of bits can be achieved by physical changes (for example by sublimation or diffusion) or by chemical changes (for example photochromicity, isomedzation or thermal decomposition) by laser irradiation in such recording materials.

Substituted phthalocyanines are an important class of dyes for use in such WORM systems, since they have high NIR absorption in the region from 700 to 900 nm if they have appropriate peripheral substitution depending on the central metal atom.

EP-A-0373 643 describes poly-alkoxy- and halogen-substituted phthalocyanines whose long-wave absorption maximum is at approx. from 740 to 820 nm. These compounds have either an inadequate refractive index and inadequate reflectivity at 780 nm or have unsatisfactory solubilities in organic solvents for spin-coating processes.

In order to overcome these solubility problems, in particular for spin-coating processes, U.S. Pat. No. 5,064,951 proposes P(V)-substituted naphthalocyanines which have a broad absorption band between 700 nm and 800 nm, the absorption maximum generally being on the long-wave side of the band. These compounds generally have a refractive index at 780 nm which is inadequate for practical purposes and are not sufficiently sensitive.

EP-A-0 513 370 describes soluble, halogenated, tetra-alkoxy-substituted phthalocyanines whose alkoxy groups contain bulky radicals. The absorption maxima of the compounds described therein are at approx. from 700 to 730 nm and have a molar absorption coefficient of $>100\,000$ $l \cdot mol^{-1} \cdot cm^{-1}$. These properties allow optical discs produced using these compounds to achieve a sufficiently high refractive index at 780 nm and good sensitivity.

A further prerequisite for high sensitivity is that the decomposition temperature must be in a favourable region, preferably below about 300° C. In order to lower the decomposition point, EP-A-0 600 427 proposes adding decomposition accelerators, for example ferrocene. However, the presence of decomposition accelerators can have an undesired adverse effect on the systems to which these additives are added.

In addition to the absorption properties and the photochemical stability, these substituted phthalocyanines must have sufficiently good solubility in organic solvents, since the absorption layer of optical storage materials is frequently applied in a spin-coating process using solutions. Recommended solvents in, for example, EP-A-0 511 598 are nonpolar solvents, such as saturated or unsaturated hydrocarbons. This solubility in hydrocarbons is achieved by lipophilic substituents, corresponding to the compounds proposed in EP-A-0 513 370.

However, it is known from the process for the production of compact discs (CDs) that dye solutions of this type must be freshly prepared daily, since dye associates can form, resulting in recrystallization and precipitation and ultimately unusable products.

A further problem in the production of optical recording materials is the control of the amount of dye settling in pits in the carrier. In order to obtain the most even films possible, it is therefore frequently necessary to add flow-control agents to the dye solution, which can in turn impair the reflection and sensitivity.

If relatively polar solvents are used, which can form relatively strong van der Waals forces or possibly hydrogen bridges, the problem of control of the amount of dye in the pits can also be solved without flow-control agents. The optimum flow properties can be achieved by adjusting the polarity of the solvent, in particular when alcohols or esters can be used concomitantly. This allows the producer of optical recording materials more opportunities for process optimization during production.

The present invention provides phthalocyanines which are substituted by phosphorus-containing groups and have many surprising properties. For example, these phthalocyanines substituted by phosphorus-containing groups are readily soluble, have no tendency to form associates, have an absorption maximum at approx. from 700 to 735 nm with a high molar absorption coefficient of $>100,000$ l/mol.cm and have a lower decomposition temperature than comparable phthalocyanines which are not substituted by phosphorus-containing groups. The structure of the absorption band is relatively narrow and the refractive index at 780 nm is high, allowing good contrast to be achieved between the written and unwritten states. The products have advantageous, low melting points or are amorphous in solid form. The introduction of a phosphorus-containing group allows the polarity of the compounds to be modified within a broad range, which opens up more opportunities for solvent selection. The shelf life of the solutions is good, so that relatively large amounts of stock solutions can be stored over an extended period without association and recrystallization and economic processing is possible. If the novel phthalocyanines substituted by phosphorus-containing groups are employed together with a decomposition accelerator, it may be possible to reduce the amount of the latter.

The invention relates to phthalocyanines and metal complexes thereof with divalent metals or divalent oxo metals which contain at least one phosphorus-containing substituent bonded to the peripheral carbon skeleton via the phosphorus atom.

The compounds preferably conform to the structural formula $(G)_k$-A-$(Q)_l$ where A is a phthalocyanine or a metal complex thereof with a divalent metal or a divalent oxo metal, G is a phosphorus-containing substituent, and Q represents further substituents as defined below. The index k is a number from 1 to 16, and l, independently of k, is 0 or a number from 1 to 15, with the proviso that the sum of k and l is a number less than or equal to 16.

Preferably 1 to 4 and particularly preferably 1 to 3 phosphorus-containing substituents are bonded to the peripheral carbon skeleton.

The peripheral carbon skeleton preferably contains a total of 4–16 substituents, particularly preferably 5–10 substituents.

The preferences listed below apply to the divalent metal atoms or divalent oxo metals of the phthalocyanine metal complexes.

The phosphorus-containing substituent is preferably selected from the group consisting of —$PR_1R_2$, —$P(X)R_3$, —$P(X)(Y)$, —$PZR_4R_5$, —$PZ(X)R_6$, and —$PZ(X)(Y)$, where $R_1$, $R_2$, $R_3$, $R_4$, $R_5$ and $R_6$, independently of one another are linear or branched $C_1$–$C_{12}$alkyl, $C_3$–$C_{12}$alkenyl or $C_3$–$C_{12}$alkynyl, which is unsubstituted or substituted by OH, halogen, $C_1$–$C_{12}$alkoxy, $COOR_7$, CN, phenyl or naphthyl, or are $C_3$–$C_8$cycloalkyl, phenyl or naphthyl which is unsubstituted or substituted by OH, halogen, $C_1$–$C_{12}$alkoxy, $COOR_7$ or CN;

X and Y, independently of one another, are —$OR_8$, —$SR_9$ or —$NR_{10}R_{11}$;

Z is O, S, Se or He;

$R_7$ is linear or branched $C_1$–$C_{12}$alkyl, $C_3$–$C_{12}$alkenyl or $C_3$–$C_{12}$alkynyl;

$R_8$ and $R_9$, independently of one another, are an alkali metal cation, $NH_4^+$, hydrogen, linear or branched $C_1$–$C_{12}$alkyl, $C_3$–$C_{12}$alkenyl or $C_3$–$C_{12}$alkynyl, which is unsubstituted or substituted by OH, halogen, $C_1$–$C_{12}$alkoxy, $COOR_7$, CN, phenyl or naphthyl, or are $C_3$–$C_8$-cycloalkyl, phenyl or naphthyl which is unsubstituted or substituted by OH, halogen, $C_1$–$C_{12}$alkoxy, $COOR_7$ or CN; and $R_{10}$, and $R_{11}$, independently of one another, are hydrogen, linear or branched $C_1$–$C_{12}$alkyl, $C_3$–$C_{12}$alkenyl or $C_3$–$C_{12}$alkynyl which is unsubstituted or substituted by OH, halogen, $C_1$–$C_{12}$alkoxy, $COOR_7$, CN, phenyl or naphthyl, or are $C_3$–$C_8$cycloalkyl, phenyl or naphthyl which is unsubstituted or substituted by OH, halogen, $C_1$–$C_{12}$alkoxy, $COOR_7$ or CN.

Examples of linear or branched $C_1$–$C_{12}$alkyl radicals are methyl, ethyl and various positional isomers of propyl, butyl, pentyl, hexyl, heptyl, octyl, nonyl, decyl, undecyl or dodecyl.

Examples of $C_3$–$C_{16}$alkenyl radicals are propenyl, butenyl, pentenyl, hexenyl, heptenyl, octenyl, nonenyl, decenyl, undecenyl or dodecenyl with their vadous positional isomers.

Examples of $C_3$–$C_{16}$alkynyl radicals are propynyl, butynyl, pentynyl, hexynyl, heptynyl, octynyl, nonynyl, decynyl, undecynyl, dodecynyl, tridecynyl, tetradecynyl, pentadecynyl or hexadecynyl with their various positional isomers.

Halogen is, for example, fluorine, chlorine, bromine or iodine.

$C_1$–$C_{12}$alkoxy is, for example, methoxy, ethoxy and various positional isomers of propoxy, butoxy, pentoxy, hexyloxy, heptyloxy, octyloxy, nonyloxy, decyloxy, undecyloxy or dodecyloxy.

$C_3$–$C_8$Cycloalkyl is, for example, cyclopropyl, dimethylcyclopropyl, cyclobutyl, cyclopentyl, methylcyclopentyl, cyclohexyl, cycloheptyl or cyclooctyl.

Alkali metal cations are, for example, $Li^+$, $Na^+$ or $K^+$.

Z is preferably O or S, very particularly preferably O.

$R_1$, $R_2$, $R_3$, $R_4$, $R_5$ and $R_6$ are, preferably, independently of one another, linear or branched, unsubstituted $C_1$–$C_{12}$alkyl, $C_3$–$C_{12}$alkenyl, $C_3$–$C_{12}$alkynyl, $C_3$–$C_8$cycloalkyl, phenyl or naphthyl.

$R_1$, $R_2$, $R_3$, $R_4$, $R_5$ and $R_6$ are particularly preferably, independently of one another, linear or branched, unsubstituted $C_1$–$C_8$alkyl, $C_3$–$C_8$alkenyl, $C_3$–$C_8$alkynyl, $C_3$–$C_8$cycloalkyl or phenyl.

$R_7$ is preferably linear or branched, unsubstituted $C_1$–$C_{12}$alkyl.

$R_8$ and $R_9$ are preferably, independently of one another, an alkali metal cation, $NH_4^+$, hydrogen, linear or branched, unsubstituted $C_1$–$C_{12}$alkyl, $C_3$–$C_{12}$alkenyl or $C_3$–$C_{12}$alkynyl, $C_3$–$C_8$cycloalkyl or phenyl, particularly preferably $C_1$–$C_6$alkyl, $C_3$–$C_8$cycloalkyl or phenyl.

$R_{10}$ and $R_{11}$ are preferably, independently of one another, linear or branched, unsubstituted $C_1$–$C_{12}$alkyl, $C_3$–$C_{12}$alkenyl or $C_3$–$C_{12}$alkynyl, $C_3$–$C_8$cycloalkyl or phenyl, particularly preferably linear or branched $C_1$–$C_6$alkyl.

A preferred subgroup of phthalocyanines and metal complexes thereof are compounds of the formula I in which Me is a divalent metal atom or a divalent oxo metal or 2 hydrogen atoms, $R_{12}$ to $R_{27}$ are, independently of one another, —$PR_1R_2$, —$P(X)R_3$, —$P(X)(Y)$, —$PZR_4R_5$, —$PZ(X)R_6$, —$PZ(X)(Y)$, hydrogen, halogen; —OH, halogen; linear or branched $C_1$–$C_{12}$alkyl, $C_3$–$C_{12}$alkenyl, $C_3$–$C_{12}$alkynyl, $C_1$–$C_{12}$alkoxy, or $C_1$–$C_{12}$alkylthio which is unsubstituted or substituted by OH, halogen, $C_1$–$C_{12}$alkoxy, $COOR_7$, CN, phenyl or naphthyl; $C_3$–$C_8$cycloalkyl, phenyl, naphthyl, phenoxy, thiophenyl, naphthoxy or thionaphthyl which is unsubstituted or substituted by OH, halogen, $C_1$–$C_{12}$alkoxy, $COOR_7$ or CN; or are —$COOR_{28}$, —$CONR_{29}R_{30}$, —$SO_3R_{31}$, —$SO_2NR_{32}R_{33}$, —$SiR_{34}R_{35}R_{36}$ or —$NR_{37}R_{38}$, where $R_{28}$ to $R_{38}$, independently of one another, are hydrogen, linear or branched $C_1$–$C_{12}$alkyl, $C_3$–$C_{12}$alkenyl or $C_3$–$C_{12}$alkynyl which is unsubstituted or substituted by OH, halogen, $COOR_7$, CN, phenyl or naphthyl, or are $C_3$–$C_8$cycloalkyl, phenyl or naphthyl which is unsubstituted or substituted by OH, halogen, $C_1$–$C_{12}$alkoxy, $COOR_7$ or CN; with the proviso that at least one of the substituents $R_{12}$ to $R_{27}$ is a phosphorus-containing substituent selected from the group consisting of —$PR_1R_2$, —$P(X)R_3$, —$P(X)(Y)$, —$PZR_4R_5$, —$PZ(X)R_6$, —$PZ(X)(Y)$, where $R_1$–$R_6$, X, Y and Z and their preferences are as defined above.

Me as a divalent metal atom is preferably Cu(II), Zn(II), Fe(II), Ni(II), Ru(II), Rh(II), Pd(II), Pt(II), Mn(II), Mg(II), Be(II), Ca(II), Ba(II), Cd(II), Hg(II), Sn(II), Co(II) or Pb(II), or Me as a divalent oxo metal is preferably VO, MnO or TiO. Very particular preference is given to Zn(II), Sn(II), Cu(II), Ni(II), Co(II), Pb(II), Pd(II) or VO.

$R_{12}$ to $R_{27}$ are preferably, independently of one another, hydrogen, halogen, linear or branched, unsubstituted $C_1$–$C_{12}$alkyl, $C_3$–$C_{12}$alkenyl, $C_3$–$C_{12}$alkynyl, $C_1$–$C_{12}$alkoxy or $C_1$–$C_{12}$alkylthio, phenyl, phenoxy or thiophenyl.

$R_{12}$ to $R_{27}$ are preferably, independently of one another, hydrogen, halogen, linear or branched, unsubstituted $C_4$–$C_{10}$alkyl, $C_4$–$C_{10}$alkenyl, $C_4$–$C_{10}$alkynyl or $C_4$–$C_{10}$alkoxy, very particularly preferably hydrogen, Br, Cl or linear or branched, unsubstituted $C_4$–$C_{10}$alkoxy.

$R_{28}$ to $R_{38}$ are preferably, independently of one another, hydrogen, linear or branched, unsubstituted $C_1$–$C_{12}$alkyl, $C_3$–$C_{12}$alkenyl or $C_3$–$C_{12}$alkynyl, $C_3$–$C_8$-cycloalkyl, phenyl or naphthyl, particularly preferably hydrogen or $C_1$–$C_{12}$alkyl.

In a preferred subgroup of metal complexes of phthalocyanines, $R_1$ to $R_6$, independently of one another, are $C_1$–$C_4$alkyl or phenyl, X and Y, independently of one another, are —$OR_8$ or —$NR_{10}R_{11}$, Z is O, Me is Pd, VO, Cu or Ni, in particular Pd, VO or Cu, and $R_{12}$ to $R_{27}$, independently of one another, are hydrogen, Br or linear or branched, unsubstituted $C_4$–$C_{10}$alkoxy.

The total number of substituents on the peripheral carbon skeleton is preferably from 4 to 10.

Particular preference is given to metal complexes of phthalocyanines in which the phosphorus-containing substituents are radicals of the formulae II–VI:

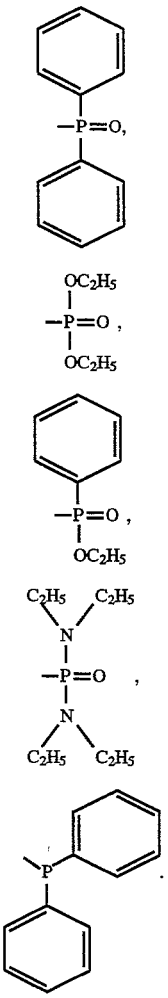

The novel compounds can be prepared analogously to processes known per se. For example, phthalocyanines substituted by phosphorus-containing groups can be prepared by condensation of phthalic acids, phthalic arthydrides, phthalimides, phthalic diamides, diiminodihydroisoindolines or phthalodinitriles substituted by phosphorus-containing groups by generally known synthetic methods, as described, for example, by F. H. Moser, A. L Thomas, The Phthalocyanines, Volume II, CRC Press, Inc., Boca Raton, Florida, 1983.

The invention further relates to a process for the preparation of phthalocyanines and divalent metal complexes or divalent oxo metal complexes thereof by reacting a phthalodinitrile or diiminodihydroisoindoline which contains a phosphorus-containing substituent, or a mixture of phthalodinitdles or diiminodihydroisoindolines at least one of which contains a phosphorus-containing substituent, and each phthalodinitdle or diiminodihydroisoindoline may, independently of one another, contain further substituents, if desired in the presence of a metal salt or oxo metal salt.

Preference is given to a process for the preparation of phthalocyanines and metal complexes thereof of the formula I by reacting a compound of the formula VII or VIII

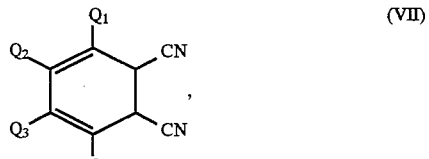

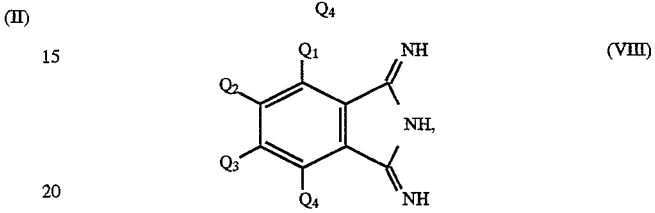

or a mixture of 2 to 4 of these compounds, if desired in the presence of a metal salt, where $Q_1$ to $Q_4$, independently of one another, are —$PR_1R_2$, —$P(X)R_3$, —$P(X)(Y)$, —$PZR_4R_5$, —$PZ(X)R_6$, —$PZ(X)(Y)$, hydrogen, OH, halogen; $C_1$–$C_{12}$alkyl, $C_3$–$C_{12}$alkenyl, $C_3$–$C_{12}$alkynyl, $C_1$–$C_{12}$alkoxy, or $C_1$–$C_{12}$alkylthio which is unsubstituted or substituted by OH, halogen, $C_1$–$C_{12}$alkoxy, $COOR_7$, CN, phenyl or naphthyl; $C_3$–$C_8$cycloalkyl, phenyl, naphthyl, phenoxy, thiophenyl, naphthoxy or thionaphthyl which is unsubstituted or substituted by OH, halogen, $C_1$–$C_{12}$alkoxy, $COOR_7$ or CN; or are $-COOR_{28}$, —$CONR_{29}R_{30}$, —$SO_3R_{31}$, —$SO_2NR_{32}R_{33}$, —$SiR_{34}R_{35}R_{36}$ or —$NR_{37}R_{38}$, in which $R_1$ to $R_7$ and $R_{28}$ to $R_{38}$ are as defined above, with the proviso that at least one compound of the formula VII or VIII carries at least one substituent $Q_1$ to $Q_4$ selected from the group of phosphorus-containing substituents consisting of —$PR_1R_2$, —$P(X)R_3$, —$P(X)(Y)$, —$PZR_4R_5$, —$PZ(X)R_6$, —$PZ(X)(Y)$, where $R_1$–$R_6$, X, Y and Z are as defined above.

Depending on the number of components employed, a mixture of various α- or β- substituted positionally isomeric phthalocyanines is obtained.

The definitions and preferences given above for Me apply to the metals or oxo metals in the salts.

Preference is given to metal salts in which the anion is derived from a monobasic or dibasic inorganic acid, a $C_1$–$C_{12}$carboxylic acid or a $C_5$–$C_{12}$-β-diketone.

Suitable inorganic acids are in particular HCl, HBr, $H_2SO_4$, $HNO_3$ and $HClO_4$. Examples of suitable $C_1$–$C_{12}$carboxylic acids are formic acid, acetic acid, propionic acid, the various isomers of butyric acid, valeric acid and caproic acid. Examples of suitable $C_5$–$C_{12}$-β-diketones are acetylacetone, hexane-2,4-dione, heptane-3,5-dione, heptane-2,4-dione, and the various positional isomers of octane-, nonane-, decane-, undecane- and dodecane-β-diones.

The particularly preferred metal salt is Pd(II)Cl$_2$, Cu(II)Cl$_2$, Zn(II)Cl$_2$, Ni(II)Cl$_2$, Cu(II) acetylacetonate or V(III) acetylacetonate.

Very particular preference is given to Pd(II)Cl$_2$, CU(II)Cl$_2$ and Ni(II)Cl$_2$.

The condensation reaction is preferably carried out in a solvent mixture of nitrobenzene, nitrotoluene or nitroxylene and at least an equimolar amount of urea, based on the compounds of the formula VII or VIII.

The novel compounds can also be prepared by reacting phthalocyanines substituted by a leaving group, or metal complexes thereof, with a phosphorus compound in the presence of a metal catalyst analogously to methods which are known in general terms. Suitable such methods are given, for example, in Houben-Weyl, Methoden der Organischen Chemie [Methods of Organic Chemistry], Volumes 12/1, 12/2, E1 and E2, Georg Thieme Verlag, Stuttgart, and in particular the publication by Y. Xu et al., Synthesis 1984/9, 781–2 (1984), the latter describing the use of tetrakis[tdphenylphosphine]palladium as catalyst in toluene as solvent.

Preference is given here to reacting halogenated phthalocyanines, whose halogen group serves as leaving group, with phosphorus compounds. It has been found, completely surprisingly, that a significantly better yield can be achieved in this reaction if it is carded out in the presence of a palladium(II) complex in a highly polar solvent.

The preferred polar solvent is dimethylformamide (DMF). Examples of other suitable highly polar solvents are those having a dielectric constant $\epsilon \geq 25$, for example ethylene carbonate, dimethyl sulfoxide, sulfolane and in particular amides such as formamide, N-methylformamide, acetamide, N-methylacetamide, N,N'-dimethylacetamide, N-methylpropionamide, pyrrolidone, N-methylpyrrolidone (NMP) and 1,1,2,2-tetramethylurea.

The palladium(II) complex used is preferably $PdCl_2$/triphenylphosphine. Other suitable catalysts, for example tetrakis(tdphenylphosphine)palladium, are known per se and are described in the abovementioned literature. It may also be advantageous to employ phosphorus compounds of other transition metals.

The invention therefore furthermore relates to a process for the preparation of phthalocyanines or metal complexes thereof by reacting a phthalocyanine or a metal complex thereof containing at least one halogen substituent as leaving group with a phosphorus-containing compound.

Preference is given to a process for the preparation of phthalocyanines or metal complexes thereof of the formula I by reacting a phthalocyanine or a metal complex thereof containing at least one halogen substituent as leaving group with a phosphorus-containing compound selected from the group consisting of $PR_1R_2R_3$, $P(X)_2R_3$, $P(X)_2(Y)$, $P(X)R_1R_2$, $P(X)_2OH$, where $R_1$ to $R_6$, X Y and Z are as defined above, in the presence of a catalyst.

Particular preference is given to a process for the preparation of phthalocyanines or metal complexes thereof of the formula I by reacting a phthalocyanine or a metal complex thereof containing at least one halogen substituent as leaving group with a phosphorus-containing compound in dimethylformamide and in the presence of palladium(II) chloride and triphenylphosphine.

The corresponding intermediates, the phosphorus-substituted phthalic acids, phthalic anhydrides, phthalimides, phthalic diamides, diiminodihydroisoindolines and phthalodinitriles, can be prepared by substitution reactions of appropriately functionalized starting materials, preferably bromides, with phosphorus compounds by methods known in general terms, for example as described in Houben-Weyl, Methoden der Organischen Chemie [Methods of Organic Chemistry], Volumes 12/1, 12/2, E1 and E2, Georg Thieme Verlag, Stuttgart.

The invention also relates to a material for optical recording and storage of information, in which at least one storage layer (2) of a phthalocyanine compound or metal complexes thereof according to claim 1 is applied to a transparent, dielectric carrier material (1).

The thickness of the storage layer (2) can be from 10 nm to 1000 nm.

The material can contain an additional reflection layer, which is applied, for example, to the storage layer. This can have a thickness of from 10 nm to 50 µm.

Particularly suitable reflective materials for the reflection layer are metals which reflect well the laser radiation used for recording and reproduction, for example the metals from the third, fourth and fifth main groups and the sub-groups of the Periodic Table of the Elements. Particularly suitable are Al, In, Sn, Pb, Sb, Bi, Cu, Ag, Au, Zn, Cd, Hg, Sc, Y, La, Ti, Zr, Hf, V, Nb, Ta, Cr, Mo, W, Fe, Co, Ni, Ru, Rh, Pd, Os, Ir, Pt and the lanthanide metals Ce, Pr, Nd, Pm, Sm, Eu, Gd, Tb, Dy, Ho, Er, Tm, Yb and Lu. Owing to the high reflectivity and ease of production, a reflection layer of aluminium or gold is particularly preferred.

The uppermost layer, for example the reflection layer or the layer of a phthalocyanine or a metal complex thereof, depending on the layer structure, is expediently provided with a protective coating, which can have a thickness of from 0.1 to 100 µm, preferably 0.1 to 50 µm, particularly preferably from 0.5 to 15 µm. Suitable protective materials are principally plastics, which are thinly applied to the carrier or the uppermost layer either directly or with the aid of adhesion layers. It is expedient to select mechanically and thermally stable plastics which have good surface properties and can furthermore be modified, for example written. These can be either thermosets or thermoplastics. Preference is given to radiation-cured (for example with UV radiation) protective coatings, which are particularly simple and economical to produce. A large number of radiation-curable materials is known. Examples of radiation-curable monomers and oligomers are acrylates and methacrylates of diols, triols and tetrols, polyimides made from aromatic tetracarboxylic acids and aromatic diamines containing $C_1$–$C_4$alkyl groups in at least two ortho-positions to the amino groups, and oligomers containing dialkylmaleimidyl groups, for example dimethylmaleimidyl groups.

Examples of suitable carriers are metals, metal alloys, glasses, minerals, ceramics, thermosetting plastics and thermoplastics. The carrier can have a thickness of from 0.01 mm to 1 cm, preferably from 0.1 mm to 0.5 cm. Preferred carriers are glasses and homopoiymeric and copolymeric plastics. Examples of suitable plastics are thermoplastic polycarbonates, polyamides, polyesters, polyacrylates and polymethacrylates, polyurethanes, polyolefins, polyvinyl chloride, polyvinylidene fluoride, polyimides, thermosetting polyesters and epoxy resins.

The recording materials to be used in accordance with the invention can be produced by processes known per se, it being possible to use different coating methods depending on the materials used and their mode of functioning.

Examples of suitable coating processes are dipping, casting, brushing, knife coating and spin coating, and vapour-deposition processes, which are carded out in high vacuum. If, for example, casting processes are used, solutions in organic solvents are generally used. When solvents are used, it must be ensured that the carriers used are insensitive to these solvents. Suitable coating processes are described, for example, in EP-A-0 401 791.

The metallic reflection layers are preferably applied by vacuum vapour deposition. The material to be applied is first introduced into a suitable vessel, which, if desired, is provided with resistance heating, and then placed in a vacuum chamber. The carrier to be coated is inserted into a holder above the vessel containing the material to be evaporated. This holder is constructed in such a way that the carrier can, if desired, be rotated (for example at 50 rpm) and heated. The vacuum chamber is evacuated to from about $1.3 \cdot 10^{-5}$ to 1.3·10$^{-6}$ mbar (10$^{-5}$ to 10$^{-6}$ mmHg), and the heating is set so that the temperature of the material to be evaporated rises to its evaporation temperature. The evaporation is continued until the layer to be deposited has the desired thickness. Depending on the system structure, the organic recording compound is applied first, followed by the reflecting layer, or vice versa. If desired, the application of a reflecting layer can be omitted.

Owing to the high adhesion to the carrier, the sputtering technique is particularly preferred for application of the metallic reflection layer. The material to be applied (for example aluminium) in the form of a plate is used as a target electrode, while the carder is attached to the counterelectrode. First, the vacuum chamber is evacuated to about 10$^{-6}$ mbar and inert gas, for example argon, is then introduced to about 10$^{-3}$ mbar. A high direct or radio-frequency voltage of several kV, if desired using permanent magnets ("magnetron sputtering"), is applied between the target electrode and the counterelectrode in order to generate an Ar$^+$ plasma. The metal particles sputtered (knocked out) from the target electrode by the Ar$^+$ ions are deposited on the substrate evenly and with strong adhesion. Coating is complete within a few tens of seconds to several minutes, depending on the target materials, sputtering method and sputtering conditions. This technique is described in detail in textbooks (for example W. Kern and L. Vossen, "Thin Film Processes", Academic Press, 1978).

The structure of the novel recording material depends principally on the reading method; known operating principles are measurement of the change of transmission or reflection. If the recording material is constructed in accordance with the change in light transmission, the following structure, for example, is suitable: transparent carrier/ recording layer (if desired multiple layers) and, if expedient, transparent protective coating. The light for recording and for reading can be incident either on the carder side or on the recording layer or, if present, the protective layer side, the light detector always being on the opposite side.

If the recording material is constructed in accordance with the change in reflection, the following structures, for example, can be used: transparent carrier/recording layer (if desired multiple layers)/reflection layer and, if expedient, protective coating (not necessarily transparent) or carrier (not necessarily transparent)/reflection layer/recording layer and, if expedient, transparent protective coating. In the former case, the light is incident on the carrier side, while in the latter case the radiation is incident on the recording layer side or, if present, on the protective coating side. In both cases, the light detector is on the same side as the light source. The first-mentioned structure of the recording material to be used in accordance with the invention is generally preferred.

Examples of suitable lasers are commercially available diode lasers, in particular semiconductor diode lasers, for example GaAsAl, InGaAlP or GaAs lasers having a wavelength of 780, 650 or 830 nm respectively, or He/Ne lasers (633 nm) and argon lasers (514 nm). The recording can be carried out pointwise with the aid of a light modulator.

The novel process enables storage of information with high reliability and stability. The information is distinguished by very good mechanical and thermal stability and by high light stability and sharp edge zones. Particularly advantageous is the surprisingly high signal/noise ratio of carrier material to information marking, which allows error-free reading.

The reading of information takes place by measurement of the absorption by the reflection process or transmission process using laser radiation, it being particularly advantageous that laser radiation of the wavelengths used for the recording can be used, i.e. there is no need to use a second laser unit. In a preferred embodiment, the recording and reading of the information take place at the same wavelength. During reading, use is generally made of low-energy lasers whose radiation intensity is reduced, for example, by from ten- to fifteen-fold compared with the laser radiation used for the recording. The information on the recording material used in accordance with the invention can be read one or more times. The change in the absorption spectrum or the stored information can be detected with a photodetector using a low-energy laser. Suitable photodetectors comprise PIN photodiodes and microscope spectrophotometers (for example ®UMSP80 from Carl Zeiss), which enable the spectral changes to be measured by means of transmission or absorption and in particular reflection.

The novel information-containing material is, in particular, an optical information material of the WORM type. It can be used, for example, as playable CDs (compact discs), as a storage material for computers or as an identity and security card, or for the production of holograms.

The invention therefore furthermore relates to the use of compounds and the material for optical recording and storage of information.

The examples below illustrate the invention in greater detail.

A) Preparation of starting materials

EXAMPLE A1: 4-Diphenylphosphoryltris 4.14 g (20 mmol) of 4-bromophthalodinitrile (prepared as described by A. A. Shapovalov et al., SU 1057491, A1) and 0.12 g (1 mmol) of nickel(II) chloride are melted in a 25 ml three-neck flask fitted with gas-inlet tube, Vigreux column, distillation attachment and dropping funnel, in an oilbath at 170° C. with stirring and under a gentle stream of argon. 5.52 g (24 mmol) of ethyl diphenylphosphinite are added dropwise over the course of 15 minutes, and the mixture is subsequently stirred for 6 hours. The reaction mixture is cooled, diluted with 100 ml of ethyl acetate, washed three times with 25 ml of saturated NaCl solution, dried over magnesium sulfate, filtered and evaporated. The brown oil, which still contains starting material, is purified by flash chromatography (eluent hexane:ethyl acetate=1:1), giving 2.3 g (35% of theory) of a clear, colourless, viscous oil whose NMR and MS data agree with the title compound.

EXAMPLE A2: Tetra-(α-2,4-dimethyl-3-pentoxy) copper phthalocyanine 100.0 g (0.41 mol) of 3-(2,4-dimethyl-3-pentoxy) phthalodinitrile, 14.0 g (0.1 mol) of copper(II) chloride, 49.6 g (0.82 mol) of urea and 2.0 g (2% by weight) of ammonium molybdate are introduced into 410 ml of nitrobenzene, and the mixture is warmed to 160° C. under an argon atmosphere with stirring and then stirred at this temperature for 5 hours. The mixture is subsequently cooled to room temperature, diluted with toluene and filtered through kieselguhr. The filtrate is evaporated to dryness at 100° C./10$^{-1}$ mbar. The residue is dissolved in 1 l of toluene and filtered through 600 g of silica gel using toluene as eluent. The filtrate is evaporated, and the residue is stirred up in 1.5 l of methanol, filtered, washed with methanol and dried overnight at 60° C./165 mbar, giving 99.5 g (94% of theory) of a green-blue solid having a $\lambda_{max}$(NMP=N-methylpyrrolidone) of 712 nm (ε=197,680 l·mol$^{-1}$·cm$^{-1}$).

EXAMPLE A3: Tetra(α-2,4-dimethyl-3-pentoxy) palladium phthalocyanine

Tetra(α-2,4-dimethyl-3-pentoxy)palladium phthalocyanine is prepared analogously to Example A2, with copper(II) chloride being replaced by palladium(II) chloride.

EXAMPLE A4: Brominated tetra(α-2,4-dimethyl-3-pentoxy)palladium phthalocyanine 10 g (9.3 mmol) of tetra(α-2,4-dimethyl-3-pentoxy) palladium phthalocyanine are introduced into 100 g of chlorobenzene and 50 g of water. 7.4 g (46.5 mmol) of bromine in 2 g of chlorobenzene are added dropwise at 40° C. over the course of 10 minutes under an argon atmosphere and with stirring, and the mixture is subsequently stirred at 60° C. for 1 hour. The reaction mixture is cooled, diluted with 100 ml of chlorobenzene, washed once with 50 ml of aqueous 3% $NaHSO_3$, dried over $MgSO_4$, filtered and evaporated. The residue is dissolved in toluene and filtered through 50 g of silica gel with toluene. The filtrate is evaporated to 80 ml and subsequently added dropwise to 700 ml of methanol. The precipitate is filtered off, washed with methanol and dried overnight at 60° C./165 mbar, giving 11.6 g (87.9% of theory) of a green powder having a $\lambda_{max}$ of 724 nm (NMP), ($\epsilon$=160,520 $l \cdot mol^{-1} \cdot cm^{-1}$) and a bromine content of 24.2%. The solubility of the product is 1.23 g/100 ml in methanol, 1.77 g/100 ml in ethanol, 2.42 g/100 ml in 2-methoxyethanol and 9.34 g/100 ml in dibutyl ether. The thermal behaviour is analysed thermogravimetrically, the onset of decomposition occurring at 282° C. and 20% weight loss being reached at 312° C.

EXAMPLE A5: Brominated tetra(α-2,4-dimethyl-3-pentoxy)copper phthalocyanine

Tetra(α-2,4-dimethyl-3-pentoxy)copper phthalocyanine is prepared analogously to Example A4.

EXAMPLE A6: Mono-β-bromotris(α-2,4-dimethyl-3-pentoxy)copper phthalocyanine 1.45 g (6 mmol) of 3-(2,4-dimethyl-3-pentoxy) phthalodinitrile and 0.49 g (2 mmol) of 4-bromophthalodinitrile are heated at 150° C. for 4 hours with stirring together with 0.52 g (2 mmol) of copper(II) acetylacetonate, 0.96 g (16 mmol) of urea and 40 mg (2% by weight) of ammonium molybdate in 10 ml of nitrobenzene in a 50 ml three-neck flask fitted with reflux condenser, magnetic stirrer, thermometer and argon inlet/outlet. The mixture is subsequently cooled to RT and transferred onto 50 g of silica gel in a glass suction filter, and the product is eluted with hexane/ethyl acetate=10:1. The filtrate is evaporated and dried at 100° C. in HV, giving 1.1 g (55% of theory) of a blue solid having a bromine content of 7.72%. UV spectrum (NMP):$\lambda_{max}$=708 nm.

EXAMPLE A7: Mono-β-bromotris(α-2,4-dimethyl-3-pentoxy)tin phthalocyanine 10.53 g (43.5 mmol) of 3-(2,4-dimethyl-3-pentoxy) phthalodinitrile and 3 g (14.5 mmol) of 4-bromophthalodinitrile are refluxed for 5.5 hours with stirring together with 1.97 g (14.5 mmol) of zinc(II) chloride, 8.8 g (58 mmol) of 1,8-diazabicyclo[5.4.0]undec-7-ene (DBU) and 270 ml of 1-pentanol in a 500 ml three-neck flask fitted with reflux condenser, magnetic stirrer, thermometer and argon inlet/outlet. The mixture is subsequently cooled to RT, filtered through a filter aid and evaporated. The residue is filtered through 250 g of silica gel with toluene, and the blue fraction is evaporated, giving 7.1 g (49% of theory) of a blue powder having a $\lambda_{max}$ of 705 nm (NMP) and a bromine content of 8.11%.

EXAMPLE A8: Mono-β-bromotris(α-2,4-dimethyl-3-pentoxy)phthalocyanine 1.2 l of ethylene glycol monomethyl ether are introduced into a 2.5 l multineck flask fitted with thermometer, anchor stirrer, reflux condenser and nitrogen inlet/outlet and warmed to 50° C. 11.4 g (1.64 mol) of lithium powder are subsequently added in portions under an inert atmosphere and at the same time the reaction solution is cooled so that the temperature does not exceed 60° C. 30 g (0.123 mol) of 3-(2,4-dimethyl-3-pentoxy)phthalodinitrile and 8.55 g (41.3 mmol) of 4-bromophthalodinitrile are then added, and the mixture is stirred under reflux for 22 hours. The reaction mixture is cooled to 40° C., 910 ml of acetic acid are added dropwise over the course of 15 minutes, and the mixture is stirred at this temperature for 30 minutes. The mixture is subsequently evaporated, the residue is filtered through 220 g of silica gel with hexane/ethyl acetate 5:1, and the blue fraction is evaporated, giving 17.0 g (44% of theory) of a blue powder having a $\lambda_{max}$ of 731/709 nm (NMP) and a bromine content of 4.09%.

B) Preparation of novel phthalocyanines

EXAMPLE B1: Mono-β-diphenylphosphoryltris-(α-2,4-dimethyl-3-pentoxy)copper phthalocyanine 5.1 g (21 mmol) of 3-(2,4-dimethyl-3-pentoxy) phthalodinitrile and 2.3 g (7 mmol) of 4-diphenylphosphanyloxyphthalodinitrile are heated at 155° C. for 4.5 hours with stirring together with 1.8 g (7 mmol) of copper(II) acetylacetonate, 3.4 g (56 mmol) of urea and 0.15 g (2% by weight) of ammonium molybdate in 20 ml of nitrobenzene in a 50 ml three-neck flask fitted with reflux condenser, magnetic stirrer, thermometer and argon inlet/outlet. The mixture is subsequently cooled to RT and transferred onto 100 g of silica gel in a glass suction filter, and the remaining starting material is eluted with toluene. The product is eluted with ethyl acetate. The filtrate is evaporated and dried at 100° C. in a high vacuum. The residue is slurried in methanol, filtered and dried overnight at 60° C./165 mbar, giving 2.0 g (26% of theory) of a blue solid having a phosphorus content of 1.86%. UV spectrum (NMP):$\lambda_{max}$= 709 nm.

EXAMPLE B2: Mono-β-diethoryphosphoryltris(α-2,4-dimethyl-3-pentoxy)copper phthalocyanine 0.5 g of the compound from Example A6, 56 mg (0.048 mmol) of tetrakis(triphenylphosphine)palladium and 50 ml of mesitylene are heated to 155° C. under a gentle stream of argon with stirring in a 100 ml three-neck flask fitted with gas-inlet tube, Vigreux column, distillation attachment, thermometer and dropping funnel. 0.24 g (1.45 mmol) of triethyl phosphite are subsequently added dropwise over the course of 10 minutes. The mixture is then stirred for 3 hours, cooled and transferred onto 50 g of silica gel in a glass suction filter, and the starting material present is eluted with toluene. The product is subsequently eluted with ethyl acetate. The filtrate is evaporated and dried at 100° C. in a high vacuum, giving 0.1 g (20% of theory) of a blue solid. UV spectrum (NMP) :$\lambda_{max}$=706 nm. Phosphorus content=3.29%.

EXAMPLE B3: Mono-β-phenyl-ethylphosphoryl(α-2,4-dimethyl-3-pentoxy)copper phthalocyanine 0.5 g of the compound of Example A6, 56 mg (0.048 mmol) of tetrakis(triphenylphosphine)palladium and 50 ml of mesitylene are heated to 155° C. under a gentle stream of argon with stirring in a 100 ml three-neck flask fitted with gas-inlet tube, Vigreux column, distillation attachment, thermometer and dropping funnel. 0.29 g (1.45 mmol) of diethyl benzenephosphonite are subsequently added dropwise over the course of 10 minutes. The mixture is stirred for 3.5 hours, then cooled and transferred onto 50 g of silica gel in a glass suction filter, and the starting material still present is eluted with toluene. The product is subsequently eluted with ethyl acetate. The filtrate is evaporated and dried at 100° C. in a high vacuum, giving 0.15 g (30% of theory) of a blue solid. UV spectrum (NMP):$\lambda_{max}$=708 nm. Phosphorus content=2.93%.

EXAMPLE B4: Mono-β-diphenylphosphoryltris(α-2,4-dimethyl-3-pentoxy)copper phthalocyanine 5.0 g of the compound from Example A6, 620 mg (0.54 mmol) of tetrakis(triphenylphosphine)palladium and 120 ml of mesitylene are heated to 160° C. under a gentle stream of argon with stirring in a 250 ml three-neck flask fitted with gas-inlet tube, Vigreux column, distillation attachment, thermometer and dropping funnel. 3.7 g (16.1 mmol) of ethyl diphenylphosphonite are subsequently added dropwise over the course of 20 minutes. The mixture is stirred at 180° C. for 4.5 hours, then cooled and transferred onto 100 g of silica gel in a glass suction filter, and the starting material still present is eluted with toluene. The product is subsequently eluted with ethyl acetate. The filtrate is evaporated, and the residue is slurried in 100 ml of methanol, filtered, washed with methanol and dried overnight at 60° C./165 mbar, giving 1.0 g (20% of theory) of a blue solid. UV spectrum (NMP):$\lambda_{max}$=709 nm. Phosphorus content=3.16%.

EXAMPLE B5: Brominated tetra(α-2,4-dimethyl-3-pentoxy)palladium phthalocyanine containing diethyl phosphonato groups 2 g of brominated tetra(α-2,4-dimethyl-3-pentoxy) palladium phthalocyanine (bromine content 18.2%), prepared as described in Example A4, 59 mg (0.46 mmol) of nickel(II) chloride and 50 ml of mesitylene are heated to an oil-bath temperature of 170° C. under a gentle stream of argon with stirring in a 100 ml three-neck flask fitted with gas-inlet tube, Vigreux column, distillation attachment, thermometer and a dropping funnel. 1.14 g (6.84 mmol) of triethyl phosphite are subsequently added dropwise over the course of 20 minutes. The mixture is stirred for 5 hours, then cooled and transferred onto 60 g of silica gel in a glass suction filter, and the starting material still present is eluted with toluene.

The product is subsequently eluted with ethyl acetate. The filtrate is evaporated and dried at 120° C. in a high vacuum, giving 0.64 g (30% of theory) of a blue-green solid. UV spectrum (NMP):$\lambda_{max}$=706 nm. Phosphorus content=2.50%, bromine content=10.8%.

EXAMPLE B6: Brominated tetra(α-2,4-dimethyl-3-pentoxy)palladium phthalocyanine containing diethyl phosphonato groups 2 g of brominated tetra(α-2,4-dimethyl-3-pentoxy) palladium phthalocyanine (bromine content 22.5%), prepared as described in Example A4, 0.32 g (0.28 mmol) of tetrakis(triphenylphosphine)palladium, 0.85 g (6.19 mmol) of diethyl phosphite, 0.63 g (6.19 mmol) of triethylamine and 50 ml of mesitylene are heated to 90° C. under a gentle stream of argon with stirring in a 100 ml three-neck flask fitted with thermometer, reflux condenser, nitrogen inlet/outlet and magnetic stirrer. The mixture is stirred for 24 hours, then cooled and transferred onto 60 g of silica gel in a glass suction filter, and the starting material still present is eluted with toluene. The product is subsequently eluted with hexane/ethyl acetate 1:1. The filtrate is evaporated, and the residue is dried overnight at 60° C./165 mbar, giving 0.33 g (16% of theory) of a blue-green solid. UV spectrum (NMP):$\lambda_{max}$=720 nm. Phosphorus content=2.13%.

EXAMPLE B7: Brominated tetra(α-2,4-dimethyl-3-pentoxy)palladium phthalocyanine containing diethyl phosphonato groups 2 g of brominated tetra(α-2,4-dimethyl-3-pentoxy) palladium phthalocyanine (bromine content 28.5%), prepared as described in Example A4, 12 mg (0.072 mmol) of palladium dichloride, 75 mg of 0.288 mmol) of triphenylphosphine and 50 ml of dimethylformamide are heated to reflux under a gentle stream of argon with stirring in a 100 ml three-neck flask fitted with thermometer, septum, reflux condenser, nitrogen inlet/outlet and magnetic stirrer. 3.56 g (21.45 mmol) of triethyl phosphite are added dropwise over the course of 15 minutes. The mixture is subsequently kept under reflux for 4 hours, then cooled and evaporated in a rotary evaporator. The residue is dissolved in toluene and transferred onto 60 g of silica gel in a glass suction filter, and the starting material still present is eluted with hexane/ethyl acetate 25:1. The product is subsequently eluted with hexane/ethyl acetate 1:1. The filtrate is evaporated, and the residue is dried overnight at 60° C./165 mbar, giving 1.2 g (57% of theory) of an amorphous blue-green solid. UV spectrum (NMP):$\lambda_{max}$=721 nm. The thermal behaviour is analysed thermogravimetrically, the onset of decomposition being at 265° C., and 20% weight loss being achieved at 294° C. The solubility of the product is 1.45 g/100 ml in methanol, 4.64 g/100 ml in ethanol, 13.15 g/100 ml in 2-methoxyethanol and 10.73 g/100 ml in dibutyl ether.

EXAMPLE B8: Brominated tetra(α-2,4-dimethyl-3-pentoxy)palladium phthalocyanine containing diethyl phosphonato groups 12.5 g of brominated tetra(α-2,4-dimethyl-3-pentoxy) palladium phthalocyanine (bromine content 23.4%), prepared as described in Example A4, 80 mg (0.45 mmol) of palladium dichloride, 472 mg (1.8 mmol) of triphenylphosphine and 140 ml of dimethylformamide are heated to reflux under a gentle stream of argon with stirring in a 250 ml three-neck flask fitted with thermometer, septum, reflux condenser, nitrogen inlet/outlet and magnetic stirrer. 18.2 g (105 mmol) of triethyl phosphite are added dropwise over the course of 15 minutes. The mixture is subsequently kept under reflux for 6½ hours, then cooled and evaporated in a rotary evaporator. The residue is dissolved in 50 ml of methylene chloride, and 12 g of silica gel are added. The mixture is evaporated, and the residue is transferred onto 100 g of silica gel in a glass suction filter. The starting material still present is eluted with hexane/ethyl acetate 25:1. The product is subsequently eluted with hexane/ethyl acetate 1:1. The filtrate is evaporated, and the residue is dried overnight at 60° C./165 mbar, giving 10 g of an amorphous blue-green solid, which is dissolved in 50 ml of tetrahydrofuran and is precipitated by dropwise addition of 75 ml of water. The reprecipitated product is washed 5× with 100 ml of water in each case and dried overnight at 60° C./30–40 mbar, giving 8.83 g of a dark-green powder. UV spectrum (NMP):$\lambda_{max}$=721 nm (ε=149,450 l·mol$^{-1}$·cm$^{-1}$).

Phosphorus content=2.91%, bromine content=14.15%.

EXAMPLE B9: Tetra(α-2,4-dimethyl-3-pentoxy)palladium phthalocyanine containing ethyl phenylphosphinate groups 2 g of brominated tetra(α-2,4-dimethyl-3-pentoxy) palladium phthalocyanine (bromine content 18.2%), prepared as described in Example A4, 94 mg (0.73 mmol) of nickel(II) chloride and 20 ml of mesitylene are heated to an oil-bath temperature of 160° C. under a gentle stream of argon with stirring in a 100 ml three-neck flask fitted with gas-inlet tube, Vigreux column, distillation attachment, thermometer and dropping funnel. 0.98 g (5.02 mmol) of diethyl benzenephosphonite are subsequently added dropwise over the course of 20 minutes. The mixture is stirred for 4.75 hours, then cooled and evaporated at 120° C. in a high vacuum. The residue is dissolved in toluene and transferred onto 100 g of silica gel in a glass suction filter, and the starting material still present is eluted with toluene. The product is subsequently eluted with ethyl acetate. The filtrate is evaporated and dried at 120° C. in a high vacuum, giving 0.3 g (15% of theory) of a blue-green solid. UV spectrum (NMP):$\lambda_{max}$=708 nm. Phosphorus content=3.25%, bromine content=7.94%.

EXAMPLE B10: Brominated tetra(α-2,4-dimethyl-3-pentoxy)palladium phthalocyanine containing diphenylphosphoryl groups 2 g of brominated tetra(α-2,4-dimethyl-3-pentoxy) palladium phthalocyanine (bromine content 19.1%), prepared as described in Example A4, 0.55 g (0.48 mmol) of tetrakis(triphenylphosphine)palladium and 50 ml of mesitylene are heated to an oil-bath temperature of 180° C. under a gentle stream of argon with stirring in a 100 ml three-neck flask fitted with gas-inlet tube, Vigreux column, distillation attachment, thermometer and dropping funel. 3.3 g (14.34 mmol) of ethyl diphenylphosphinite are subsequently added dropwise over the course of 10 minutes. The mixture is stirred for 4 hours, then cooled and transferred onto 100 g of silica gel in a glass suction filter, and the starting material still present is eluted with toluene. The product is subsequently eluted with ethyl acetate. The filtrate is evaporated and dried at 120° C. in a high vacuum, giving 0.2 g (10% of theory) of a blue-green solid. UV spectrum (NMP):$\lambda_{max}$= 718 nm. Phosphorus content=2.43%, bromine content= 12.81%.

EXAMPLE B11: Tetra(α-2,4-dimethyl-3-pentoxy) copper phthalocyanine containing diethyl phosphonato groups 4 g of brominated tetra(α-2,4-dimethyl-3-pentoxy)copper phthalocyanine (bromine content=16.6%), prepared as described in A5, 0.96 g (0.831 mmol) of tetrakis (triphenylphosphine)palladium and 100 ml of mesitylene are heated to an oil-bath temperature of 180° C. under a gentle stream of argon with stirring in a 250 ml three-neck flask fitted with gas-inlet tube, Vigreux column, distillation attachment, thermometer and dropping funnel. 4.14 g (24.93 mmol) of triethyl phosphite are subsequently added dropwise over the course of 20 minutes. The mixture is stirred for 2.5 hours, and cooled, and the mesitylene is evaporated at 100° C. in a high vacuum. The residue is dissolved in toluene and transferred onto 100 g of silica gel in a glass suction filter, and the starting material still present is eluted with toluene. The product is subsequently eluted with ethyl acetate. The filtrate is evaporated and dried at 120° C. in a high vacuum, giving 2.6 g (65% of theory) of a blue-green solid. UV spectrum (NMP):$\lambda_{max}$=721 nm. Phosphorus content=3.23%, bromine content=8.72%.

EXAMPLE B12: Brominated tetra(α-2,4-dimethyl-3-pentoxy)palladium phthalocyanine containing bis (N,N'-diethylamide phosphonato groups 2 g of brominated tetra(α2,4-dimethyl-3-pentoxy) palladium phthalocyanine (bromine content=22.5%), prepared as described in Example A4, 0.65 g (0.56 mmol) of tetrakis(tdphenylphosphine)palladium and 50 ml of mesitylene are heated to an oil-bath temperature of 180° C. under a gentle stream of argon with stirring in a 100 ml three-neck flask fitted with gas-inlet tube, Vigreux column, distillation attachment, thermometer and dropping funnel. 3.5 g (16.89 mmol) of ethyl bis(N,N-diethyl)phosphoramidate are subsequently added dropwise over the course 30 minutes. The mixture is stirred for 4 hours, then cooled and transferred onto 100 g of silica gel in a glass suction filter, and the starting material still present is eluted with toluene. The product is subsequently eluted with ethyl acetate. The filtrate is evaporated, and the residue is dried at 60° C./165 mbar, giving 0.15 g (8% of theory) of a blue-green solid. UV spectrum (NMP):$\lambda_{max}$=722 nm. Phosphorus content=4.25%, bromine content=15.89%.

EXAMPLE B13: Brominated tetra(α-2,4-dimethyl-2-pentoxy)palladium phthalocyanine containing diphenylphosphino groups 1.48 g (5.63 mmol) of triphenylphosphine, 0.12 g (16.9 mmol) of lithium powder and 15 ml of tetrahydrofuran (freshly dried over Na) are introduced into a 50 ml three-neck flask fitted with nitrogen inlet/outlet, reflux condenser, thermometer and magnetic stirrer, and the mixture is stirred at RT for 3 hours. 0.52 g (5.63 mmol) of t-butyl chloride is subsequently added. The orange-red suspension is refluxed for 40 minutes and then cooled, and the supernatant solution is transferred into a 100 ml three-neck flask fitted with thermometer, reflux condenser, dropping funnel, nitrogen inlet/outlet and magnetic stirrer and again heated to reflux. 2 g of brominated tetra(α-2,4-dimethyl-3-pentoxy) palladium phthalocyanine (bromine content 22.5%), prepared as described in Example A4, dissolved in 20 ml of abs. THF, are added dropwise over the course of 20 minutes. The mixture is allowed to react for 2 hours and then cooled, and the solvent is evaporated. The residue is dissolved in toluene, washed with water and dried over magnesium sulfate. The solution is filtered and transferred onto 100 g of silica gel in a glass suction filter, the product is eluted with toluene. The filtrate is evaporated, and the residue is dried overnight at 60° C./165 mbar, giving 1.8 g (90% of theory) of a blue-green solid. UV spectrum (NMP):$\lambda_{max}$=722 nm. Phosphorus content=5.72%, bromine content=6.52%.

EXAMPLE B14: Mono-β-diethoryphosphoryltris (α-dimethyl-3-pentoxy)zinc phthalocyanine 7.0 g (7 mmol) of the compound from Example A7, 62 mg (0.35 mmol) of palladium(II) chloride, 0.37 g (1.4 mmol) of triphenylphosphine and 175 ml of dimethylformamide are heated to 155° C. under a gentle stream of argon with stirring in a 250 ml three-neck flask fitted with gas-inlet tube, Vigreux column, distillation attachment, thermometer, magnetic stirrer and dropping funnel. 3.53 g (21.3 mmol) of triethyl phosphite are subsequently added dropwise over the course of 20 minutes. The mixture is stirred for 8 hours, then cooled and evaporated. The residue is transferred onto 100 g of silica gel in a glass suction filter, and the starting material still present is eluted with hexane/ethyl acetate 25:1. The product is then eluted with hexane/ethyl acetate 1:1. The filtrate is evaporated, giving 1.5 g (20% of theory) of a blue solid. UV (NMP):$\lambda_{max}$=707 nm. Phosphorus content=3.59%.

EXAMPLE B15: Mono-β-diethylphosphonyloxytris (α-2,4-dimethyl-3-pentoxy)palladium 17.0 g (18.2 mmol) of the compound from Example A8, 160 mg (0.91 mmol) of palladium(II) chloride, 0.95 g (3.63 mmol) of triphenylphosphine and 400 ml of dimethylformamide are heated to 155° C. under a gentle stream of argon with stirring in a 1 l three-neck flask fitted with gas-inlet tube, Vigreux column, distillation attachment, thermometer, magnetic stirrer and dropping funnel. 4.33 g (26.1 mmol) of tdethyl phosphite are subsequently added dropwise over the course of 25 minutes. The mixture is stirred for 11 hours, then cooled and evaporated. The residue is transferred onto 220 g of silica gel in a glass suction filter, and the starting material still present is eluted with hexane/ethyl acetate 25:1. The product is eluted with hexane/ethyl acetate 1:1. The filtrate is evaporated, giving 2.4 g (13.3% of theory) of a blue solid. UV (NMP):$\lambda_{max}$=723 nm. Phosphorus content= 3.19%.

C) Use examples

EXAMPLE C1: Optical recording material

A 2% solution in methylcyclohexane is prepared of the compound prepared as in Example B6. After complete dissolution, the solution is filtered through a 0.2 μm Teflon filter. The dye solution is subsequently spin-coated at 150 rpm for 8 seconds onto a 1.2 mm thick grooved polycarbonate plate. The speed is increased to 1200 rpm, causing excess dye solution to be spun off and forming a uniform solid layer. The polycarbonate plate with the recording layer is dried at 60° C. for 10 minutes. A 14 μm thick reflection layer of gold is vapour-deposited onto the recording layer in a vacuum vapour deposition unit. A 13 p.m thick UV-curable acrylate-containing polymer protective coating from Dainippon Ink (®Daicure SD-17) is spin-coated on top and cured by exposure.

Signals corresponding to the EFM-CD (Eight to Fourteen Modulation Compact Disc format) are written in the recording layer using a semiconductor diode emitting at 780 nm with a power of 8 mW and a linear speed of 1.2 to 1.4 m/s. The signals recorded in this way have lengths of from 0.9 μm to 3.3 μm at intervals of from 0.8 μm to 3.5 μm and exhibit an eye diagram which meets specifications.

The recorded signals are subsequently read using a commercially available CD reader with a power of 0.5 mW at 780 nm. The recording material has very good reproduction quality.

What is claimed is:

1. Phthalocyanine or a metal complex thereof with a divalent metal or a divalent oxo metal which has at least one phosphorus-containing substituent bonded to the peripheral carbon skeleton via the phosphorus atom whereas the phosphorus-containing substituent is selected from the group consisting of —$PR_1R_2$, —$P(X)R_3$, —$P(X)(Y)$, —$PZR_4R_5$, —$PZ(X)R_6$ and —$PZ(X)(Y)$, where $R_1$, $R_2$, $R_3$, $R_4$, $R_5$ and $R_6$, independently of one another, are linear or branched $C_1$–$C_{12}$-alkyl, $C_3$–$C_{12}$alkenyl, $C_3$–$C_{12}$ alkynyl, which is unsubstituted or substituted by OH, halogen, $C_1$–$C_{12}$alkoxy, $COOR_7$, CN, phenyl or naphthyl, or are $C_3$–$C_8$-cycloalkyl, phenyl or naphthyl which is unsubstituted or substituted by OH, halogen, $C_1$–$C_{12}$alkoxy, $COOR_7$ or CN, X and Y, independently of one another, are —$OR_8$, —$SR_9$ or —$NR_{10}R_{11}$;

Z is O, S, Se or He;

$R_7$ is linear or branched $C_1$–$C_{12}$alkyl, $C_{3-C12}$alkenyl or $C_3$–$C_{12}$alkynyl;

$R_8$ and $R_9$, independently of one another, are an alkali metal cation, $NH_4^+$, hydrogen, linear or branched $C_1$–$C_{12}$alkyl, $C_3$–$C_{12}$alkenyl or $C_3$–$C_{12}$alkenyl, which is unsubstituted or substituted by OH, halogen, $C_1$–$C_{12}$alkoxy, $COOR_7$, CN, phenyl or naphthyl, or are $C_3$–$C_8$-cycloalkyl, phenyl or naphthyl which is unsubstituted or substituted by OH, halogen, $C_1$–$C_{12}$alkoxy, $COOR_7$ or CN; and $R_{10}$ and $R_{11}$, independently of one another are, hydrogen, linear or branched $C_1$–$C_{12}$alkyl, $C_3$–$C_{12}$alkenyl or $C_3$–$C_{12}$alkynyl, which is unsubstituted or substituted by OH, halogen, $C_1$–$C_{12}$alkoxy, $COOR_7$, CN, phenyl or naphthyl, or are $C_3$–$C_8$-cycloalkyl, phenyl or naphthyl which is unsubstituted or substituted by OH, halogen, $C_1$–$C_{12}$alkoxy, $COOR_7$ or CN.

2. A compound according to claim 1, which conforms to the general structural formula $(G)_k$-A-$(Q)_l$, in which A is a phthalocyanine or a metal complex thereof with a divalent metal or a divalent oxo metal, G is a phosphorus-containing substituent, Q is a further substituent, k is a number from 1 to 16, and l, independently thereof, is 0 or a number from 1 to 15, with the proviso that the sum of k and l is a number less than or equal to 16.

3. A compound according to claim 1, which has from 1 to 4 phosphorus-containing substituents G bonded to the peripheral carbon skeleton.

4. A compound according to claim 1, which has a total of 4–16 substituents bonded to the peripheral carbon skeleton.

5. A compound according to claim 1, wherein Z is O or S.

6. A compound according to claim 1, wherein $R_1$, $R_2$, $R_3$, $R_4$, $R_5$ and $R_6$, independently of one another, are linear or branched, unsubstituted $C_1$–$C_{12}$alkyl, $C_3$–$C_{12}$alkenyl, $C_3$–$C_{12}$alkynyl, $C_3$–$C_8$cycloalkyl, phenyl or naphthyl.

7. A compound according to claim 1, wherein $R_1$, $R_2$, $R_3$, $R_4$, $R_5$ and $R_6$, independently of one another, are linear or branched, unsubstituted $C_1$–$C_8$alkyl, $C_3$–$C_8$alkenyl, $C_3$–$C_{12}$alkynyl, $C_3$–$C_8$cycloalkyl or phenyl.

8. A compound according to claim 1, wherein $R_7$ is linear or branched, unsubstituted $C_1$–$C_{12}$alkyl.

9. A compound according to claim 1, wherein $R_8$ and $R_9$, independently of one another, are an alkali metal cation, $NH_4^+$, hydrogen, linear or branched, unsubstituted $C_1$–$C_{12}$alkyl, $C_3$–$C_{12}$alkenyl or $C_3$–$C_{12}$alkynyl, $C_3$–$C_8$cycloalkyl or phenyl.

10. A compound according to claim 9, wherein $R_8$ and $R_9$, independently of one another, are $C_1$–$C_6$alkyl, $C_3$–$C_8$cycloalkyl or phenyl.

11. A compound according to claim 1, wherein $R_{10}$ and $R_{11}$, independently of one another, are linear or branched, unsubstituted $C_1$–$C_{12}$alkyl, $C_3$–$C_{12}$alkenyl or $C_3$–$C_{12}$alkynyl, $C_3$–$C_8$cycloalkyl or phenyl.

12. A compound according to claim 11, wherein $R_{10}$ and $R_{11}$, independently of one another, are linear or branched, unsubstituted $C_1$–$C_6$alkyl.

13. Phthalocyanine/metal complex according to claim 1, wherein the divalent metal is Cu(II), Zn(II), Fe(II), Ni(II), Ru(II), Rh(II), Pd(II), Pt(II), Mn(II), Mg(II), Be(II), Ca(II), Sa(II), Cd(II), Hg(II), Sn(II), Co(II) or Pb(II), or the divalent oxo metal is VO, MnO or TiO.

14. A compound according to claim 13, wherein the divalent metal is Zn(II), Sn(II), Cu(II), Ni(II), Co(II), Pb(II) or Pd(II) or the divalent oxo metal is VO.

15. A compound according to claim 1, conforming to the formula I,

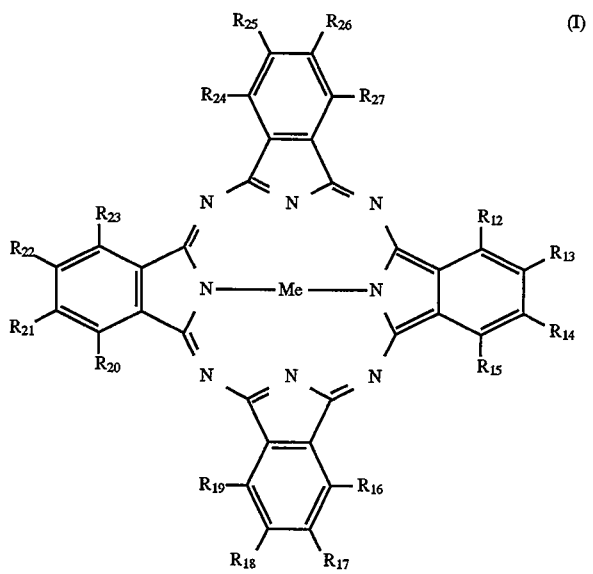

in which Me is a divalent metal atom or a divalent oxo metal or 2 hydrogen atoms, $R_{12}$ to $R_{27}$ are, independently of one another, —$PR_1R_2$, —$P(X)R_3$, —$P(X)(Y)$, —$PZR_4R_5$, —$PZ(X)R_6$, —$PZ(X)(Y)$, hydrogen, —OH, halogen; linear or branched $C_1$–$C_{12}$alkyl, $C_3$–$C_{12}$alkenyl, $C_{3-12}$alkynyl, $C_1$–$C_{12}$alkoxy, or $C_1$–$C_{12}$alkylthio which is unsubstituted or substituted by OH, halogen, $C_1$–$C_{12}$alkoxy, $COOR_7$, CN, phenyl or naphthyl; $C_3$–$C_8$cycloalkyl, phenyl, naphthyl, phenoxy, thiophenyl, naphthoxy or thionaphthyl which is unsubstituted or substituted by OH, halogen, $C_1$–$C_{12}$alkoxy, $COOR_7$ or CN; or are —$COOR_{28}$, —$CONR_{29}R_{30}$, —$SO_3R_{31}$, —$SO_2NR_{32}R_{33}$, —$SiR_{34}R_{35}R_{36}$ or —$NR_{37}R_{38}$, where $R_{28}$ to $R_{38}$, independently of one another, are hydrogen, linear or branched $C_1$–$C_{12}$alkyl, $C_3$–$C_{12}$alkenyl or $C_3$–$C_{12}$alkynyl which is unsubstituted or substituted by OH, halogen, CN, phenyl or naphthyl, or are $C_3$–$C_8$cycloalkyl, phenyl or naphthyl which is unsubstituted or substituted by OH, halogen, $C_1$–$C_{12}$alkoxy, $COOR_7$ or CN;

with the proviso that at least one of the substituents $R_{12}$ to $R_{27}$ is a phosphorus-containing substituent selected from the group consisting of —$PR_1R_2$, —$P(X)R_3$, —$P(X)(Y)$, —$PZR_4R_5$, —$PZ(X)R_6$, —$PZ(X)(Y)$, where $R_1$–$R_6$, X, Y and Z are as defined in claim 5.

16. A compound according to claim 15, where $R_{12}$ to $R_{27}$, independently of one another, are hydrogen, halogen, linear or branched, unsubstituted $C_1$–$C_{12}$alkyl, $C_3$–$C_{12}$alkenyl, $C_3$–$C_{12}$alkynyl, $C_1$–$C_{12}$alkoxy, $C_1$–$C_{12}$alkylthio, phenyl, phenoxy or thiophenyl.

17. A compound according to claim 15, wherein $R_{12}$ to $R_{27}$, independently of one another, are hydrogen, halogen, linear or branched, unsubstituted $C_4$–$C_{10}$alkyl, $C_4$–$C_{10}$alkenyl, $C_4$–$C_{10}$alkynyl or $C_4$–$C_{10}$alkoxy.

18. A compound according to claim 17, wherein $R_{12}$ to $R_{27}$, independently of one another, are hydrogen, Br, Cl or linear or branched, unsubstituted $C_4$–$C_{10}$alkoxy.

19. A compound according to claim 15, wherein $R_{28}$ to $R_{38}$, independently of one another, are hydrogen, linear or branched, unsubstituted $C_1$–$C_{12}$alkyl, $C_3$–$C_{12}$alkenyl, or $C_3$–$C_{12}$alkynyl, $C_3$–$C_8$-cycloalkyl, phenyl or naphthyl.

20. A compound according to claim 19, wherein $R_{28}$ to $R_{38}$, independently of one another, are hydrogen or $C_1$–$C_{12}$alkyl.

21. A compound according to claim 15, wherein $R_1$ to $R_6$, independently of one another, are $C_1$–$C_4$alkyl or phenyl;

X and Y, independently of one another, are —$OR_8$ or —$NR_{10}R_{11}$;

Z is O;

Me is Pd, VO, Cu or Ni; and $R_{12}$ to $R_{27}$, independently of one another, are hydrogen, Br or linear or branched, unsubstituted $C_4$–$C_{10}$alkoxy.

22. A phthalocyanine/metal complex according to claim 1, wherein the phosphorus-containing substituents are radicals of the formulae II–VI

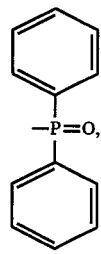

(II)

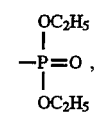

(III)

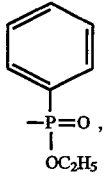

(IV)

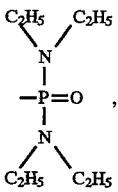

(V)

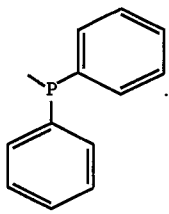

(VI)

23. A compound according to claim 15, in which Me is Pd, and the radicals $R_{12}$ to $R_{27}$ are hydrogen, bromine, 2,4-dimethyl-3-pentoxy or —$PO(OC_2H_5)_2$, where 3 of the radicals $R_{12}$ to $R_{27}$ are bromine, 2 of the radicals $R_{12}$ to $R_{27}$ are —$PO(OC_2H_5)_2$, 4 of the radicals $R_{12}$, $R_{15}$, $R_{16}$, $R_{19}$, $R_{20}$, $R_{23}$, $R_{24}$ and $R_{27}$ are 2,4-dimethyl-3-pentoxy, and the other 7 radicals $R_{12}$ to $R_{27}$ are hydrogen.

24. A compound according to claim 15, in which Me is Cu, and the radicals $R_{12}$ to $R_{27}$ are hydrogen, bromine, 2,4-dimethyl-3-pentoxy or —$PO(OC_2H_5)_2$, where 1 or 2 of the radicals $R_{12}$ to $R_{27}$ are bromine, 1 of the radicals $R_{12}$ to $R_{27}$ is —$PO(OC_2H_5)_2$, 4 of the radicals $R_{12}$, $R_{15}$, $R_{16}$, $R_{19}$, $R_{20}$, $R_{23}$, $R_{24}$ and $R_{27}$ are 2,4-dimethyl-3-pentoxy, and the other 10 or 9 radicals $R_{12}$ to $R_{27}$ are hydrogen.

25. A material for the optical recording and storage of information, in which at least one layer (2) of a compound according to claim 1 has been applied to a transparent, dielectric carrier material (1).

* * * * *